(12) United States Patent
Sobko et al.

(10) Patent No.: US 6,230,710 B1
(45) Date of Patent: May 15, 2001

(54) ELECTRICAL POWER SYSTEM FOR A SELF-CONTAINED TRANSPORTABLE LIFE SUPPORT SYSTEM

(75) Inventors: William Richard Sobko, Torrance; Thomas Wakefield Good, Oceanside; Thomas Holland Alford, Torrance, all of CA (US)

(73) Assignee: Integrated Medical Systems, Inc., Signal Hill, CA (US)

( * ) Notice: Subject to any disclaimer, the term of this patent is extended or adjusted under 35 U.S.C. 154(b) by 0 days.

(21) Appl. No.: 09/285,346

(22) Filed: Apr. 2, 1999

Related U.S. Application Data

(63) Continuation-in-part of application No. 08/667,693, filed on Jun. 21, 1996, now Pat. No. 5,975,081.

(51) Int. Cl.[7] ................................................. A61G 15/00
(52) U.S. Cl. ............................................. 128/845; 128/897
(58) Field of Search ................................... 128/845, 846, 128/869, 870; 600/21, 22; 370/85, 93, 94, 95

(56) References Cited

U.S. PATENT DOCUMENTS

| 4,161,172 | 7/1979 | Pickering ................................. 128/1 |
| 4,352,991 | 10/1982 | Kaufman .................................. 307/9 |
| 4,554,657 | * 11/1985 | Wilson .................................. 370/85 |
| 4,680,790 | 7/1987 | Packard et al. ...................... 379/432 |
| 4,715,385 | 12/1987 | Cudahy et al. ...................... 128/710 |
| 4,963,763 | * 10/1990 | Minagawa ............................. 307/35 |
| 4,981,139 | 1/1991 | Pfohl .................................... 128/671 |
| 5,111,818 | 5/1992 | Suzuki et al. ........................ 128/644 |
| 5,307,818 | 5/1994 | Segalowitz ........................... 128/696 |
| 5,331,549 | 7/1994 | Crawford, Jr. .................. 364/413.02 |
| 5,404,877 | 4/1995 | Nolan et al. ......................... 128/671 |
| 5,421,340 | * 6/1995 | Stanga ................................. 128/671 |
| 5,441,047 | 8/1995 | David et al. ......................... 128/670 |
| 5,474,574 | 12/1995 | Payne et al. ............................ 607/7 |
| 5,494,051 | 2/1996 | Schneider, Sr. ..................... 128/870 |
| 5,511,553 | 4/1996 | Segalowitz ........................... 128/696 |
| 5,590,648 | 1/1997 | Mitchell et al. ..................... 128/630 |
| 5,626,151 | * 5/1997 | Linden ................................. 128/897 |
| 5,630,238 | 5/1997 | Weismiller et al. ..................... 5/600 |
| 5,664,270 | 9/1997 | Bell et al. ............................... 5/600 |
| 5,687,717 | 11/1997 | Halpern et al. ...................... 128/630 |
| 5,749,374 | 5/1998 | Schneider, Sr. ..................... 128/870 |

FOREIGN PATENT DOCUMENTS

PCT/AU95/000477  2/1996  (WO) .

* cited by examiner

Primary Examiner—Michael A. Brown
(74) Attorney, Agent, or Firm—Stetina Brunda Garred & Brucker

(57) ABSTRACT

A switching control circuit for use in an electrical power system for a transportable life support system is disclosed. The switching control circuit provides uninterrupted power to a load of medical and utility devices by switching between one of a set of converted external power voltages and an internal power voltage outputted by a rechargeable internal power source. The power switching is effected within the time interval during which a residual voltage still remains on line due to capacitance discharge of the corresponding power converter and capacitance discharge of the main bus, resulting in uninterrupted electrical power to the load.

The switching control circuit comprises: (a) an input power select circuit for outputting a voltage selected from the group of internal and converted external power voltages; (b) a bus switch, which receives the selected voltage, for controlling the application of the selected voltage to the load; and (c) a main bus for transporting the selected voltage to the load of medical and utility devices.

22 Claims, 3 Drawing Sheets

ELECTRICAL POWER SYSTEM FOR A SELF-CONTAINED TRANSPORTABLE LIFE SUPPORT SYSTEM

RELATED APPLICATION

This patent application is a continuation-in-part patent application of U.S. Ser. No. 08/667,693, filed Jun. 21, 1996, now U.S. Pat. No. 5,975,081 and entitled SELF-CONTAINED TRANSPORTABLE LIFE SUPPORT SYSTEM, the contents of which are hereby incorporated by reference.

FIELD OF THE INVENTION

The present invention relates generally to an electrical power system which provides power to various medical devices, and more particularly to an electrical power system which receives power from an internal and various external power sources and provides uninterrupted power for use in a self-contained transportable life support system, which is utilized in the resuscitation, stabilization, and transport of medical patients such as heart attack, stroke, accident victims and battlefield casualties.

BACKGROUND OF THE INVENTION

The need for simultaneously transporting and providing necessary medical treatment to patients in emergency conditions is well known. Such need can be met with a self-contained transportable life support system which integrates various medical and utility devices into a stretcher upon which a patient is placed.

An example of such system is described in the related patent application Ser. No. 08/667,693 filed on Jun. 21, 1996, entitled SELF-CONTAINED TRANSPORTABLE LIFE SUPPORT SYSTEM.

In order to evacuate a patient from the battlefield to a remote hospital, a number of different military vehicles are commonly used. For example, a HumVee may be used to transport the patient to a helipad, where the patient is subsequently transported via a UH-60 Blackhawk or UH-1 Huey helicopter to an airfield. From the airfield, the patient is then transported typically via a C-130 or C-141 fixed wing aircraft to an airport near the remote hospital. Thus, it is desirable that such self-contained transportable life support system can draw electrical power from various external power sources, such as those which exist in these transport vehicles. It is desirable that the power connection to any external power source is designed to be foolproof, in order to prevent human error. It is also desirable that such system can be powered by a rechargeable internal power source when no external power source is available.

It is imperative that the switching from one type of power source to another does not interrupt the electrical power being delivered to the load of medical and utility devices of the life support system, so that the ongoing medical care is not impeded.

In addition, it is desirable that any failure of one medical or utility device in such life support system will not interfere with the operation of the remaining functioning devices.

The present invention discloses an electrical power system, to be used in a self-contained transportable life support system, which allows such life support system to possess the desired features discussed above.

SUMMARY OF THE INVENTION

A switching control circuit for use in an electrical power system for a transportable life support system is disclosed. The switching control circuit provides uninterrupted power to a load of medical and utility devices by switching between one of a set of converted external power voltages and an internal power voltage outputted by a rechargeable internal power source. The power switching is effected within the time interval during which a residual power voltage still remains on line due to capacitance discharge of the corresponding power converter and capacitance discharge of the load, resulting in uninterrupted electrical power to the load.

The switching control circuit comprises: (a) an input power select circuit for outputting a voltage selected from the group of internal and converted external power voltages; (b) a main bus switch, for controlling the application of the selected voltage to the load; and (c) a main bus for transporting the selected voltage to the load of medical and utility devices.

The input power select circuit monitors the active converted external voltage to determine its magnitude with respect to a threshold voltage. When the converted DC voltage is larger than a threshold voltage, the circuit selects the converted voltage instead of the rechargeable internal power source. When it falls below the threshold voltage, the circuit selects and outputs the rechargeable internal power source. This voltage selection scheme facilitates seamless switching between the rechargeable internal power source and one of the converted external power sources. External power cabling allows for the application of only one external power source at a time. Thus, only one power converter is active at a given time.

The input power select circuit preferably comprises a boost regulator circuit which creates an enhancement voltage that is greater than the selected voltage by a fixed amount of voltage and utilizes the resulting enhanced voltage to control the main bus switch. In the preferred embodiment of the invention, the boost regulator circuit creates an enhanced voltage that exceeds the selected voltage by approximately 12 volts.

The input power select circuit comprises (a) a diode OR gate for preventing contention between the converted external power source and the rechargeable internal power source; (b) a battery control circuit which compares the diode OR gate output described in (a) above with a threshold voltage and enables the rechargeable internal power source to output the internal power voltage to the bus switch when the diode OR gate output is smaller than the threshold voltage.

A converted external power voltage produced by the active power converter is approximately 6 volts greater than the threshold voltage internal to the battery control circuit. Thus, when the converted external power voltage falls below the threshold voltage, this indicates that the corresponding power converter has just been disconnected from an external power source or the power converter has failed. Capacitors residing in the power converter and capacitors residing on the main bus will hold the main bus voltage up briefly while switching to the rechargeable internal power source is accomplished.

In the preferred embodiment of the invention, the threshold voltage is set at approximately 6 volts less than the nominal value of a converted external power voltage. This allows the input power select circuit to select the rechargeable internal power source, during the brief hold up time of the main bus, while the capacitance of the corresponding power converter and the capacitance of the main bus are discharging. This results in uninterrupted electrical power to the load during the voltage switching.

The bus switch is preferably a field-effect transistor (FET) switch.

The switching control circuit also includes a main bus delay circuit for controlling turn ON of the main bus switch. The main bus delay circuit receives the rising edge of the selected voltage from the input power select circuit and controls operation of the bus switch at initial power-up of the transportable life support system. By controlling the bus switch, the main bus delay circuit delays application of the selected voltage to the main bus by a fixed amount of time at initial power-up to prevent fire hazard.

This time delay is about ten seconds. During this time delay, a brushless fan is operated to dissipate any flammable gas build-up in the transportable life support system, before main bus power is applied. This delay prevents potential fire hazard.

An electrical power system for providing uninterrupted power, by switching between different power sources, to a load of medical and utility devices in a transportable life support system, is also disclosed.

The electrical power system comprises: (a) a set of external power sources which provide different external power voltages; (b) a rechargeable internal power source which provides an internal power voltage; (c) a set of different power converters which convert the different external power voltages into converted external power voltages, one of the different power converters providing recharge power to the rechargeable internal power source; (d) a switching control circuit which receives the internal and converted external power voltages, and switches at its output between the internal power voltage and one of the converted external power voltages without power interruption to the load; and (e) a plurality of precision DC-to-DC power supplies (PPS), each of the PPS receiving the output from the switching control circuit (main bus) and outputting a voltage to provide electrical power to the medical or utility devices.

The switching control circuit of the electrical power system is as disclosed above.

The electrical power system is preferably configured such that each of the precision DC-to-DC power supplies provides electrical power to no more than one device of the load, resulting in preventing any failure of one of the devices from affecting the remaining functioning devices.

The electrical power system further comprises: (a) a main power cable for transporting electrical power from one of the external power sources to a corresponding power converter; and (b) a set of different power adapters. Each of the different power adapters couples one of the external power sources to the main power cable. Each of the different power adapters has a unique mating connector which enables connection to only one distinct type of external power sources existing on a distinct type of transport vehicles. This feature allows the power connection to be foolproof.

The different power sources are independently overcurrent-protected and comprise preferably: (a) main power converter (AC/DC converter) for receiving an input from an external AC power source; (b) a DC-to-DC converter for receiving an input from an external DC power source; and (c) a trickle charger for receiving an input from an external AC or DC power source, and for providing recharge power to the rechargeable internal power source. The rechargeable internal power source is preferably a group of battery cells. The power converters allows utilization of various external power sources, including those having U.S., European or military standards.

These, as well as other advantages of the present invention will be more apparent from the following description and drawings. It is understood that changes in the specific structure shown and described may be made within the scope of the claims without departing from the spirit of the invention.

DETAILED DESCRIPTION OF THE INVENTION

The detailed description set forth below in connection with the appended drawings is intended as a description of the presently preferred embodiments of the invention, and is not intended to represent the only forms in which the present invention may be constructed or utilized. The description sets forth the functions and the sequence of the steps for constructing and operating the invention in connection with the illustrated embodiments. It is to be understood, however, that the same or equivalent functions may be accomplished by different embodiments that are also intended to be encompassed within the spirit and scope of the invention.

The primary objective of the electrical power system is to supply electrical power to every medical device and to every utility subsystem in a self-contained transportable life support system, such as the one described in the pending patent application Ser. No. 08/667,693, in a safe, precise and efficient manner.

The centralization of power utilities allows all devices to be operated from multiple external power sources and allows communication to the respective interfaces by a single cable.

The rechargeable internal power source provides backup power to all devices in the event of loss of external power. This power switching is effected without power interruption to the load of medical devices and utility subsystems. The rechargeable internal power source supports stand-alone operations, for at least 30 minutes, during movement of a self-contained transportable life support system between locations while external power is unavailable. With the centralized electrical power system, the need to manage the recharge or replacement of batteries of each medical device or utility subsystem is eliminated, and the readiness of all devices is ensured.

In the preferred embodiment of the invention, there is no preference priority which would provide power to one device over another. All power switching is under operator control and hardwired circuit logic.

Figure 1:
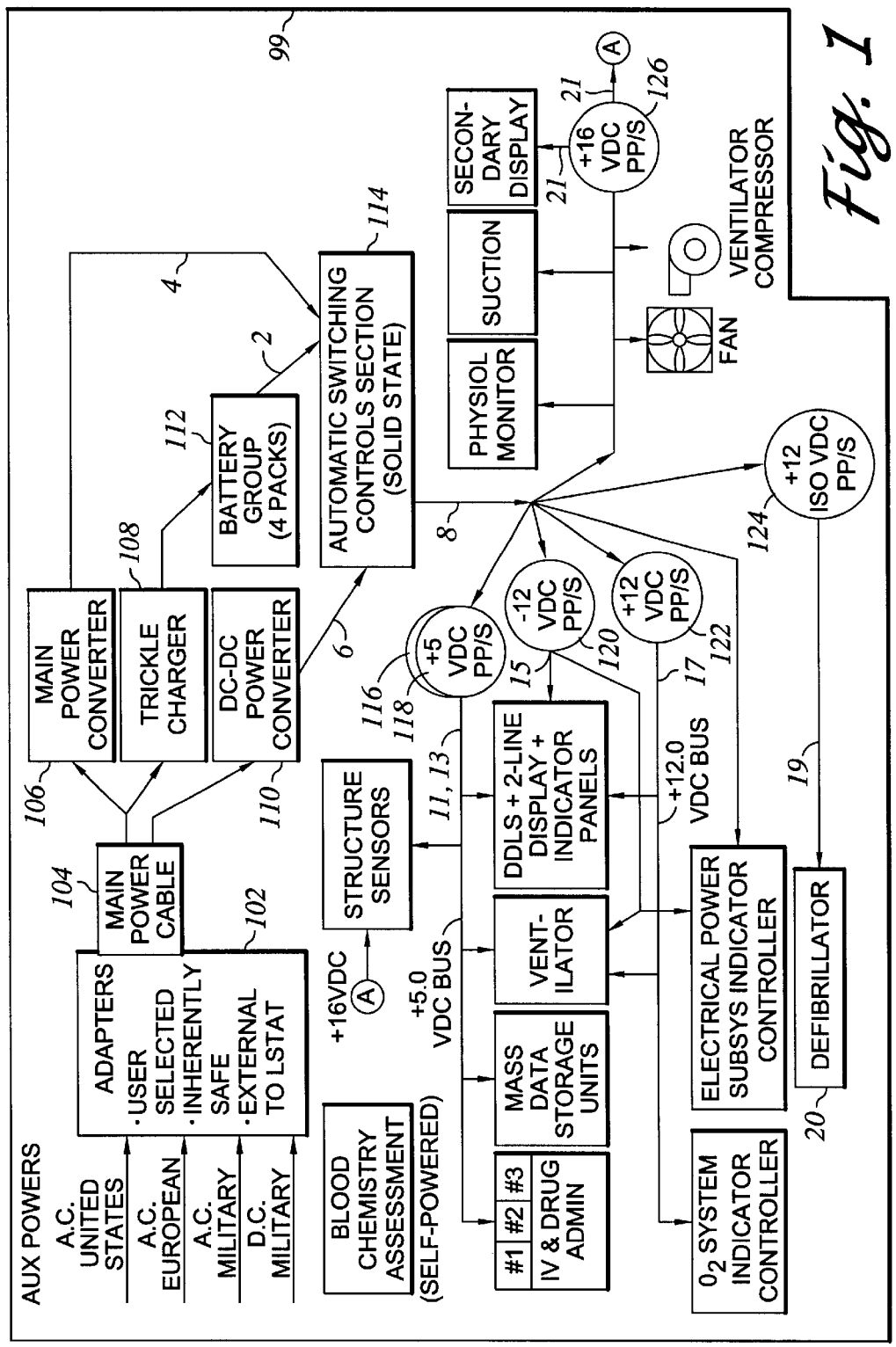
FIG. 1 illustrates the block diagram of the electrical power system of the present invention in conjunction with the power distribution in a self-contained transportable life support system.

FIG. 1 illustrates the block diagram of the electrical power system of the present invention in conjunction with the power distribution in a self-contained transportable life support system.

Referring to FIG. 1, the electrical power system of the present invention comprises a set of different power adapters 102, a main power cable 104, a main power converter (AC/DC converter) 106, a trickle charger 108, a DC-to-DC power converter 110, a group of battery cells 112, a switching control circuit 114, and six precision DC-to-DC power supplies (PPS) 116, 118, 120, 122, 124, 126.

The set of different power adapters 102 allows coupling of one of the external power sources 99 to the main power cable 104. Each of the different power adapters 102 has a unique mating connector enabling connection to one distinct type of external power sources 99 existing on a distinct type of transport vehicles. Thus, there is a unique mating connector for each of the unique combinations of external power sources and transport vehicles, resulting in a foolproof connection of external power to the transportable life support system. An operator cannot make a misconnection because a misconnected adapter will not fit.

The external power sources 99 are over-current protected by thermal circuit breakers, and comprise the following three AC sources (United States, European, and military) and one DC (military) source:

115 Volts AC +/−10% , 60 Hz +/−5 Hz, 1 phase
230 Volts AC +/−10% , 50 Hz +/−3 Hz, 1 phase
108–118/200 Volts AC, 400 Hz +/−7 Hz , any phase
25 Volts DC +/−5 Volts DC The main power cable 104 provides a hardwired power path from each of the adapters 102 to the main power converter 106, the trickle charger 108, or the DC-to-DC power converter 110, each of which outputs a voltage of approximately 28 volts DC. The main power converter 106, the trickle charger 108, and the DC-to-DC power converter 110 have built-in current limiting circuitry which protects the corresponding output from over-current.

The battery group 112 is protected from over-current by thermal circuit breakers. The battery group 112 functions as a primary power source lending portability and autonomy to a self-contained transportable life support system. The rechargeable internal power source 112 supports stand-alone operations, for at least 30 minutes, during movement of the self-contained transportable life support system between locations while external power is unavailable. The rechargeable internal power source 112 also provides backup power to all devices in the event of loss of external power.

The battery group 112 receives a small constant current from the trickle charger 108 to recharge its battery cells, and outputs an internal power voltage 2 of 28 volts DC (nominal) to the automatic switching control circuit 114. When one of the external power sources 99 is connected to the self-contained transportable life support system, the switching control circuit 114 receives the +28 volt DC (nominal) external power voltages 4 and 6 from the main power converter 106 and the DC-to-DC power converter 110, respectively, and outputs +28 volts DC (nominal) on its main bus 8. When there is no external power, the automatic switching control circuit 114 switches to receive the +28 volt DC internal power voltage 2, and outputs a voltage of +28 volts DC on its main bus 8. This power switching is effected while a residual voltage still remains on the main bus 8, resulting in no power interruption to the load of medical devices and utility subsystems. When an external power source 99 is disconnected from the life support system, electrical power is retained on the main bus 8 for several milliseconds due to the discharge of the capacitors residing within the power converter, either 106 or 110, and due to capacitors residing on the main bus 8. The automatic switching control circuit 114 is designed to take advantage of this fact, and performs power switching from an external power source to a rechargeable internal power source in less than several milliseconds.

The main bus 8 transports electrical power to the six precision DC-to-DC power supplies (PPS) 116, 118, 120, 122, 124, 126. The PPS 116 outputs a +5 volts DC to sub-bus 11 to power utility subsystems. The PPS 118 outputs a +5 volts DC to sub-bus 13 to power medical subsystems. The PPS 120 outputs a −12 volts DC to sub-bus 15. The PPS 122 outputs a +12 volts DC to sub-bus 17. The PPS 124 outputs a +12 volts DC to isolated sub-bus 19 to power the defibrillator 20. The PPS 126 outputs +16 volts DC to sub-bus 21. The six PPS 116, 118, 120, 122, 124, 126 each have a built-in over-current limiting circuitry to protect the main bus 8 from the sub-buses 11, 13, 15, 17, 19, 21. Each of the main bus and sub-buses is over-current protected from faulty medical devices and utility subsystems by their own internal current limiting.

As depicted in FIG. 1, only the defibrillator 20 is connected to a dedicated sub-bus 19 receiving power from a dedicated isolated PPS 124. However, in the preferred embodiment of the invention, each of the medical devices or utility subsystems is connected to a dedicated sub-bus receiving power from a dedicated isolated PPS. Such configuration results in preventing any failure of one medical device or subsystem from affecting the remaining functioning devices and subsystems.

Figure 2:
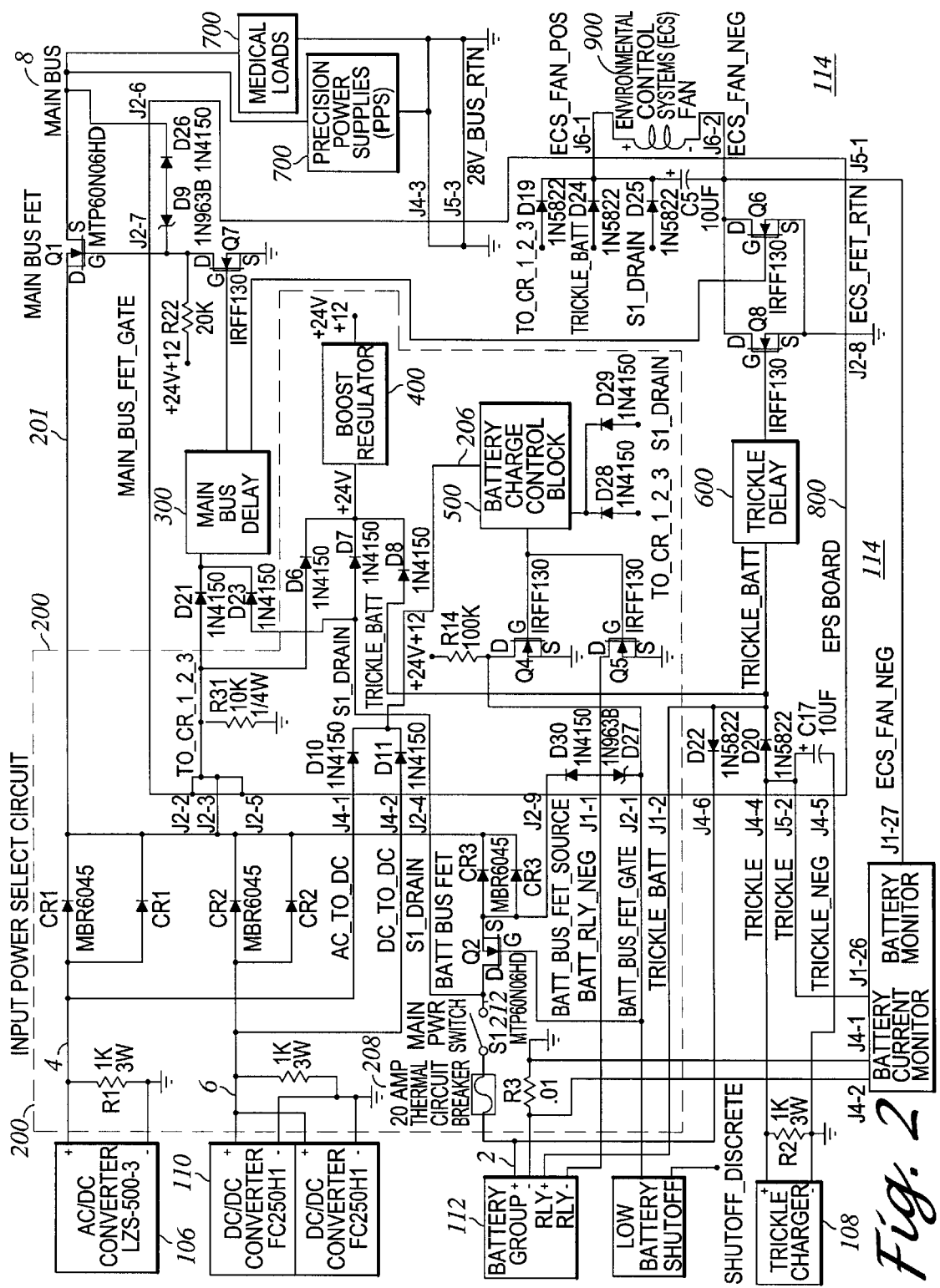
FIG. 2 is a block diagram of the switching control circuit of the present invention.

FIG. 2 shows the block diagram of the automatic switching control circuit 114 of FIG. 1. The automatic switching control circuit 114 comprises an input power select circuit 200, a main bus FET Q1, and the main bus 8. It also includes a main bus delay circuit 300, and a trickle delay circuit 600.

In addition to a configuration of diodes and FET switches, the input power select circuit 200 also includes a boost regulator circuit 400 and a battery control circuit (battery charge control block) 500.

The input power select circuit 200 receives a voltage from the group consisting of the internal and external power voltages. Only one voltage can be selected at a time. The input power select circuit 200 uses a configuration of diodes and FET switches to provide to this voltage a path to the circuit output 201.

This permits seamless switching between external power and internal battery group 112. The AC/DC converter 106 and the DC/DC converter 110 are continuously monitored by the input power select circuit 200 via the diode OR gate formed by the diode D10 and D11. The output 206 of the diode OR gate is compared to a threshold voltage internal to the battery charge control block 500. When the output 206 voltage, representing a converted external power voltage, drops below about +22.0 volts (corresponding to about +21.0V on the main bus 8, three volts higher than the 18.0V minimum for the PPS), the battery charge control block 500 makes the decision to switch on the FET Q2 by turning the control FET Q4 off. This applies +24V+12 from the boost regulator circuit 400 output to the gate of the n-channel FET Q2 through resistor R14. This applies battery group 112 voltage through the 20 amp circuit breaker 208, through the main power switch S1, through the FET Q2, through the diode CR3, and through the main bus FET Q1 to the load (medical loads and PPS) 700. When the FET Q4 is turned off, the FET Q5 is also turned off. Simultaneously with the turning on of the FET Q2, the battery group 112 configuration relay (RLY+ and RLY−) is de-energized by the turning off of the FET Q5. The de-energized relay configuration immediately sets the battery group 112 to its full output voltage mode. Thus, the full battery group 112 voltage rather than the two thirds charging voltage is applied to the load 700 when a power converter (either 106 or 110) voltage drops below approximately +22.0 volts.

Similarly, if either converter 106, 110 voltage again rises above approximately +24.0 volts, both FETs Q4 and Q5 are switched on by the battery charge control block 500. This immediately turns off the FET Q2 by grounding the gate of FET Q2 through FET Q4 that has been turned on. This results in one of the two converter 106, 110 voltages being applied through either the diodes CR1 or CR2 and through main bus FET Q1 to the main bus load 700. Simultaneously with the turning off of FET Q2, the battery group 112 configuration relay is energized through the FET Q5, which is ON, switching the battery group 112 from the full output voltage mode to the two-thirds output voltage or charging mode. The constant current trickle charger 108 then begins to charge the battery group 112 by driving a constant current through the diodes D20 and D22 into the positive terminal of the battery group 112. If the battery group 112 is configured for full output voltage mode by its de-energized configuration relay, then D22 is back biased, thus preventing the battery group 112 from being charged by the trickle charger 108.

Diodes D27 and D30 protect the gate of FET Q2 by allowing a maximum of 12.7 volts from Q2 gate to Q2 source. Similarly, diodes D9 and D26 protect the main bus FET Q1. Diodes D30 and D26 prevent back drive of the Electronic Power System (EPS) through the gate to source Zener protection diodes D27 and D9. The battery charge control block 500 is powered through either diode D28 or D29 in a diode OR gate, since either one of the power converters 106, 110 or the battery group 112 can provide the powering voltage. Similarly, the boost regulator circuit 400 is powered through diodes D6, D7, and D8, since either one of the converters 106, 110 or the battery group 112, or the trickle charger 108 can provide the powering voltage.

Figure 3:
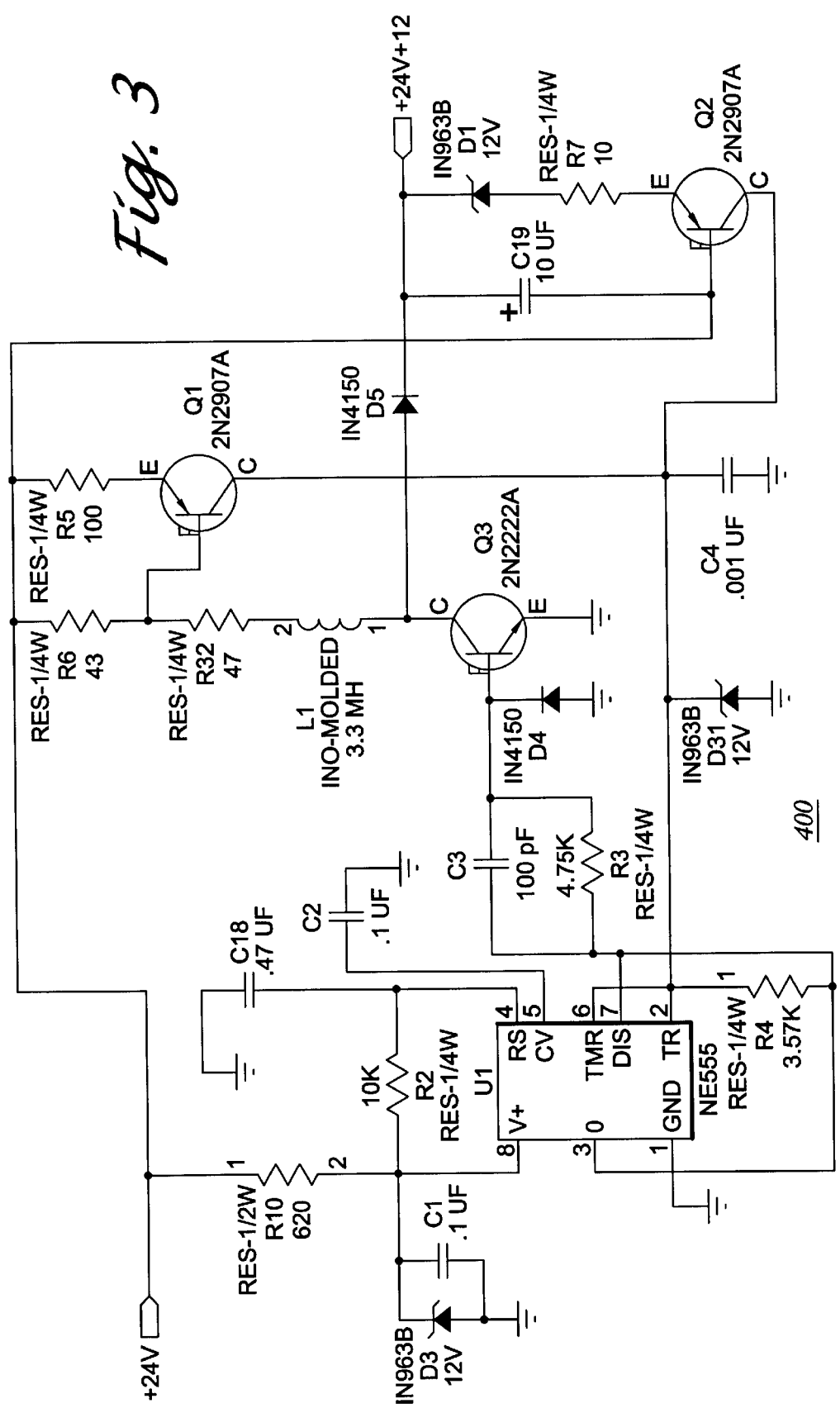
FIG. 3 is a schematic diagram of the boost circuit.

The boost regulator circuit 400, shown in more detail at FIG. 3, consists of a self tracking switch mode boost regulator that tracks 12 volts higher than the applied voltage. The applied voltage is either the trickle charger 108 voltage, the AC/DC converter 106 voltage, the DC/DC converter 110 voltage, or the battery group 112 voltage applied through the diodes D6, D7, and D8. It is a closed loop servo system that responds within milliseconds to changes in the applied voltage. It is used to enhance the n-channel FETs Q1 and Q2. Sudden step changes of voltage between the converters 106, 110, battery group 112, and trickle charger 108 are quickly compensated for. Main bus 8 voltage can vary anywhere from 18.0 volts to 36.0 volts. The boost regulator circuit 400 must track efficiently. This is especially important, when switching from a low voltage to a high voltage. For example, if the main bus voltage from a low battery group 112 is +18.0 volts, then the boost output is at +30.0 volts (18.0+12.0). If now suddenly a +30.0 volt AC/DC converter 106 is turned on, the enhancement voltage is suddenly 0.0 volts (30.0V—30.0V) and the FET Q1 begins to turn off, unless the boost regulator circuit 400 quickly responds to the change by going to +42.0 (30.0V +12.0V) volts rapidly. If the boost regulator circuit 400 is slow, a glitch in the power could occur, propagating throughout the life support system.

The diodes CR1, CR2, and CR3 form a diode OR gate for the voltages from the two converters 106, 110 and the battery group 112. This OR gate isolates the various power sources one from the other. Although each of these diodes consumes approximately 7.5 watts (15A×0.5V), they are needed to protect the life support system. If FET Q2 fails or switches inadvertently, while either converter 106, 110 is on, the various power voltages will contend with each other, causing damage to the life support system if it were not for the presence of CR1, CR2, and CR3.

The transportable life support system is vented by running an Environmental Control System (ECS) fan 900 for several seconds before applying power to the main bus load 700 via the main bus FET Q1. The transportable life support system is also vented, when only the trickle charger 108 power is first applied. The purpose of this venting is to remove oxygen or other flammable gases from the life support system before power is applied to the main bus load 700. The ECS fan is designed with a brushless DC motor to prevent fire hazard due to arcing brushes.

The main bus delay circuit 300 and the trickle delay circuit 600 provide the necessary time delays to vent the system of hazardous gases. When either one of the two converters 106, 110 or the battery group 112 is powered up as sensed by the diode D21 or D23, the main bus delay circuit 300 turns on the FETs Q7 and Q6 for a specified period of time, e.g., 10 seconds, determined by an internal RC time constant. When FET Q7 is turned on the gate of Q1 is grounded, turning the main bus FET Q1 off, thus preventing power from being delivered to the main bus load 700. Simultaneously Q6 is turned on, applying ground to the negative side of the fan motor 900. Since the positive side of the fan motor 900 is powered by either the AC/DC converter 106, the DC/DC converter 110, the battery group 112, or the trickle charger 108 through the diode OR gate consisting of D19, D24, and D25, the fan motor 900 spins until the main bus delay circuit 300 times out. After the delay times out, both the FETs Q6 and Q7 are turned off. When FET Q6 turns off, the current flow from the fan motor 900 to ground is interrupted and the fan motor 900 turns off. Simultaneously, when FET Q7 turns off, +24V+12V enhancement voltage from the boost regulator circuit 400 is applied to the gate of FET Q1 through resistor R22. This turns the main bus FET Q1 on, applying power to the main bus load 700.

The main bus delay circuit 300 does not exhibit a constant delay time. The delay is not only a function of the internal RC time constant but also of the magnitude of the voltage applied. Since the voltage applied to the main bus delay circuit 300 can vary anywhere from about 18.0 volts to 36.0 volts, the delay time can also vary significantly. When the voltage is low (e.g., 18.0 volts) the fan 900 runs slow, because of the applied low voltage, but the delay time of the main bus delay circuit 300 is longer. Similarly, when the voltage is high (e.g,. 36.0 volts) the ECS fan runs fast, because of the applied high voltage, however, the delay time of the main bus delay circuit 300 is shorter. The net result is that the volume of air displaced is roughly constant despite the variation in delay time and input voltage. The length of the delay time can be easily changed, by increasing or decreasing the RC time constant in the main bus delay circuit 300.

The trickle delay circuit 600 starts to time, when the trickle charger 108 is turned on. It turns on FET Q8, thus providing a return path to ground for the fan motor 900, which spins until the trickle delay circuit 600 times out. FET Q8 then turns off, interrupting current flow to the fan motor 900. Similar to the main bus delay circuit 300, the trickle delay circuit 600 is a function of both the internal RC time constant and the magnitude of the applied voltage from the trickle charger 108. However, the time delay and the fan speed vary in such a way as to keep the volume of air displaced relatively constant, as discussed above.

The switching time through the Battery Charge Control Block 500, the control FET (Q4), and the Batt Bus FET (Q2) must be fast enough so that the Main Bus does not glitch, before the Battery group 112 replaces the external power sources. For this reason, high speed N-channel Power MOSFETs are used for both the Batt Bus FET (Q2) and the Main Bus FET (Q1). At the 20 amp maximum current being drawn from the Main Bus, it is impractical to use hold up capacitors to hold up the Main Bus for slower switching devices such as relays. Such hold up capacitors would be too large. N-channel power MOSFETs on the other hand can switch large amounts of current in a few microseconds with no contact bounce and their channel resistance (a few milliohms) can be made lower than the contact resistance of a power relay (tens of milliohms). Relays have one advantage over MOSFETs in that there is total isolation between the input and output. This is not a problem in the system as long as power grounds and signal grounds are kept separate and not mixed.

To fully enhance most N-channel power MOSFETs requires a gate to source voltage of at least 10.0 volts but not greater than 20.0 volts. This requires a circuit that boosts the MOSFET's gate voltage at least 10.0 volts higher than the selected Main Bus voltage. Since no such voltage exists in the system, it must be created in the Boost Regulator block. The Boost Regulator 500 outputs a signal called +24V+12, which is always 12.7 volts more positive than the selected voltage. This voltage is used to fully enhance the gate of either the Main Bus FET, the Batt Bus FET, or both. The enhancement value of 12.7 volts was selected to guarantee full enhancement under component tolerances, while simultaneously staying as far away as possible from the gate/source breakdown voltage of 20.0 volts. The Batt Bus FET (Q2) and the Main Bus FET (Q1) have unique gate to source protection circuits. The power MOSFETs must be protected from failure due to overvoltage, because their reliability is essential to the safety of the patient. If something fails in the Boost Regulator, high voltages could be applied to the gates of Q1 and Q2. One way of protecting a MOSFET is by placing a Zener protection diode from gate to source to clamp overvoltages to somewhere between full enhancement (10.0 VDC) and breakdown (20.0 VDC). The problem with this approach in this particular system is that external circuitry can forward bias, such a zener, causing damage to the EPS Board 800. For this reason signal diodes D26 and D30 have been placed in series with zener diodes D9 and D27 respectively to prevent back driving the EPS board through the forward biased zeners. For example, when Q2 is ON, Battery Group 112 voltage is applied to the anode of D27 (assuming D30 is a short). The Battery Group 112 could be momentarily shorted when control MOSFET (Q4) is turned ON. There is a finite time delay from the time Q4 is turned ON and Q2 is turned OFF. During this brief time the Battery Group 112 would be shorted to ground through Q4. This could stress Q4 as well as glitch ground due to the large momentary current spike. The addition of the series signal diode (D30) alleviates this problem by preventing the protection zener from ever being forward biased.

Diodes CR1, CR2, and CR3 are necessary to prevent the selected power source from back driving or contending with the other two power sources. CR1,2,3 are Power Schottky diodes to minimize power consumption. Only one of these 3 diodes carries power at a time depending on the selected power source. There are two halves to each diode and each is capable of carrying the full load current. These halves are paralleled to increase system reliability. If one half of the diode fails, the other half will take over the full load current. Since Power Schottky diodes have a large leakage currents, 1K ohm bleeder resistors are necessary at the outputs of the AC/DC and DC/DC Converters to prevent the Battery voltage from leaking through CR1 and CR2 and then back through D10 and D11 and inadvertently exceeding the trigger threshold in the Battery Charge Control Block 500. If this happened, the Battery Charge Control Block could inadvertently turn OFF the Batt Bus FET causing a glitch in Main Bus power. The 1K value of the bleeders is low enough to keep the voltage due to leakage through D10 and D11 well below the reference threshold internal to the Battery Charge Control Block 500.

The EPS board 800 controls charging and discharging of the Battery Group 112 through the Battery Charge Control Block 500. When the AC/DC or DC/DC Converter output voltages are not present or dip below a reference threshold internal to the Battery Charge Control Block 500, control MOSFETs Q4 and Q5 are turned OFF. Q4, being OFF, applies +24V+12 from the Boost Regulator 400 through R14 to fully enhance the gate of the Batt Bus FET, Q2. This applies the full Battery voltage through the 20 amp circuit breaker, through the Main Power Switch (S1,) through Batt Bus FET (Q2), through CR3, and through the normally ON Main Bus FET (Q1) to the Main Bus. Q5, being OFF, removes the ground return for the configuration relays internal to the Battery. With no current in these relays, the Battery Group 112 is configured to full output. The whole process is fast enough to prevent glitching of the Main Bus 8 during power transfers without the need for massive hold up capacitors.

When either the AC/DC or DC/DC Converter, 106 and 110, rises above the reference threshold internal to the Battery Charge Control Block 500, control MOSFETs Q4 and Q5 are turned ON. Q4, being ON, turns OFF the Batt Bus FET thus removing the Battery Group 112 from the Main Bus 8. Q5, being ON, allows current to be driven from the Trickle Charger 108, through D20, through the internal configuration relays of the Battery and down through Q5 to ground. This actuates the Battery relays and configures the Battery Group 112 in the two-thirds of full output or charge mode. The Trickle Charger 108 then drives a constant current through D20 and D22 into the positive terminal of the Battery Group 112 and out the negative ;terminal of the Battery Group 112 to ground.

The Boost Regulator 400 consists of a self tracking flyback regulator. The schematic for the Boost Regulator is shown in FIG. 3. The input to the Boost Regulator is +24V from either the AC/DC Converter 106 or the DC/DC Converter 110, the Battery Group 112, or the Trickle Charger 108. The +24V input is derived from the diode OR of D6, D7, and D8 shown in FIG. 2. The +24V input is zenered down to +12V by D3, where it is used to power the NE555 timer (U1). U1 is configured for astable operation. The timer output (U1–3) is triggered to an active high level (12 volts), when the trigger input (U1–2) dips below one third of V+ (U1–8) (4 volts). The timer output is triggered to an active low level (0.1 volts), when the threshold input (U1–6) rises above two thirds of V+(8 volts). At power on, C4 is initially uncharged, so that trigger input (U1–2) is sitting at a low. This triggers the output of the timer IC to an active high. This active high is applied to the base of chopper transistor Q3, through the parallel combination of C3 and R3, causing Q3 to turn ON. Energy is stored in L1, when Q3 is turned ON according to the formula $\frac{1}{2}LI^2$. Q3 remains ON until C4 is charged above 8 volts (two-thirds of V+) through resistor R4. U1's output then falls low, discharging C4 through R4, while turning Q3 OFF. When Q3 turns OFF, L1 releases its stored energy to C19 and the load, through the forward biased diode, D5. Eventually, the energy from L1 will charge C19 to a voltage large enough to breakdown the 12V zener, D1, and the base emitter junction of Q2. When this happens, Q2 turns ON and charges C4 more rapidly than would have occurred had it been solely charged through R4 alone. This rapidly terminates the energy transfer from L1 to C19 by turning Q3 ON and begins anew the process of energy storage in L1. Thus the +24V+12 output of the Boost Regulator always tracks about 12.7 volts (one 12V zener drop plus one 0.7V base/emitter junction drop) above the +24V input. As the load at the output of the Boost Regulator increases, charge is pulled more rapidly from C19, requiring a more rapid replenishment of energy from L1. This causes the frequency of the U1 to increase as the load is increased.

Q1 provides overcurrent protection for the Boost Regulator 400. If for any reason inductor L1 saturates, high currents could flow through Q3 and L1 causing damage. If the current through L1 becomes too high, the voltage drop across R6 becomes high enough to breakdown the base emitter junction of Q1. This turns ON Q1, providing a current path through R5 to rapidly charge C4 above the 8.0V threshold, which drives U1's output low and thus turns Q3 OFF. This mechanism protects the Boost Regulator from inadvertent high currents by quickly terminating the ON time of Q3. D31 is a 12V zener diode that protects U1 in case the voltage at C4 rises above the input rail at V+(12.0V). D31 clamps the threshold and trigger inputs of U1 to 12V.

It is understood that the exemplary switching control circuit and electrical power system described herein and shown in the drawings represent only presently preferred embodiments of the invention. Indeed, various modifications and additions may be made to such embodiments without departing from the spirit and scope of the invention. Those skilled in the art will recognize that various other configurations are equivalent and therefore likewise suitable. Thus, these and other modifications and additions may be obvious to those skilled in the art and may be implemented to adapt the present invention for use in a variety of different applications.

What is claimed is:

1. A switching control circuit for use in an electrical power system for a transportable life support system, the switching control circuit providing uninterrupted electrical power to a load of medical and utility devices by switching between one of a set of converted external power sources, provided by one of a set of power converters, and an internal power voltage outputted by a rechargeable internal power source, the switching control circuit comprising:

(a) an input power select circuit in electrical communication with the rechargeable internal power source and with the power converters to receive the internal power voltage and the converted external power voltage, respectively, said input power select circuit monitoring the converted external voltage and then selecting and outputting said external power voltage when said external power voltage is larger than a threshold voltage, selecting and outputting the internal power voltage when said external power voltage is smaller than the threshold voltage, said selection of voltage facilitating seamless switching between the internal power voltage and one of the converted external power voltages;

(b) a main bus switch in electrical communication with the input power select circuit to receive the selected voltage, the main bus switch controlling application of the selected voltage to the load of medical and utility devices; and (c) a main bus in electrical communication with the bus switch for transporting the selected voltage to the load of medical and utility devices;

(d) wherein the main bus switch comprises a field-effect transistor switch.

2. The switching control circuit as recited in claim 1 wherein the input power select circuit comprises a boost regulator circuit for creating an enhancement voltage that is greater than the selected voltage by a fixed amount of voltage and for controlling the state of the main bus switch using the enhanced voltage.

3. The switching control circuit as recited in claim 2 wherein the boost regulator circuit creates an enhancement voltage from the selected voltage that is approximately 12 volts greater than the selected voltage.

4. The switching control circuit as recited in claim 1 wherein the input power select circuit comprises:

(a) a diode OR gate for isolating and monitoring the converted external power voltages, only one of the converted voltages being active at a given time, the diode OR gate being operative to isolate the active converted voltage from the passive converted voltage; and (b) a battery control circuit in electrical communication with the one active converted voltage through a diode OR gate, said battery control circuit comparing the diode OR gate output with a threshold voltage, and enabling the rechargeable internal power source to output the internal power voltage to said bus switch when the diode OR gate output is smaller than the threshold voltage.

5. The switching control circuit as recited in claim 1 wherein the threshold voltage, is set at approximately six volts less than nominal value of a converted external power voltage, allowing the input power select circuit to switch to select the internal power voltage while a residual voltage due to capacitance discharge of a corresponding power converter and main bus load remains on the main bus, resulting in uninterrupted electrical power to the load of medical and utility devices during voltage switching.

6. The switching control circuit as recited in claim 1 further comprises a main bus delay circuit for controlling the state of the main bus switch, the main bus delay circuit receiving the selected voltage and controlling the state of the main bus switch to delay application of the selected voltage to the main bus by a fixed amount of time at initial power-up to prevent fire hazard due to flammable gas build-up in the transportable life support system.

7. An electrical power system for providing uninterrupted power, by switching between different power sources, to a load of medical and utility devices, said load being included in a transportable life support system, the electrical power system comprising:

(a) a set of external power sources for outputting different external power voltages;

(b) a rechargeable internal power source for outputting an internal power voltage;

(c) a set of different power converters in electrical communication with the external power sources, each of the different power converters receiving one of the different external power voltages and outputting a first converted external power voltage, one of the different power converters providing recharging voltage to the rechargeable internal power source;

(d) a switching control circuit, having an input for receiving the one of internal power voltages and the converted external power voltages and for switching output between the internal power voltage and one of the converted external power voltages, said switching being effected while a residual voltage remains on the output, resulting in uninterrupted power to the load; and (e) a plurality of precision DC-to-DC power supplies (PPS), in electrical communication with the output of the switching control circuit, each of the PPS outputting a voltage to no more than one of a medical device load and a utility device load.

8. The electrical power system as recited in claim 7 further comprises:
(a) a main power cable for transporting power from one of the external power sources to a selected one of the different available power converters; and
(b) a set of different power adapters, each of the different power adapters coupling one of the external power sources to the main power cable, each of the different power adapters having a unique mating connector enabling connection to one distinct type of external power sources existing on a distinct type of transport vehicles.

9. The electrical power system as recited in claim 7 wherein the rechargeable internal power source comprises a group of battery cells.

10. The electrical power system as recited in claim 7 wherein the different power converters are independently over-current-protected and comprise:
(a) a main power converter in electrical communication with an external AC power source;
(b) a DC-to-DC converter in electrical communication with an external DC power source; and
(c) a trickle charger in electrical communication with an external AC power source and with an external DC power source, said trickle charger outputting a constant current to the rechargeable internal power source to recharge said rechargeable internal power source.

11. The electrical power system as recited in claim 7 wherein each of the precision DC-to-DC power supplies provides electrical power to no more than one device of the load of medical and utility devices, resulting in preventing any failure of one device of the load from affecting the remaining devices of the load.

12. The electrical power system as recited in claim 7 wherein the switching control circuit comprises:
(a) an input power select circuit in electrical communication with the rechargeable internal power source and with the power converters to receive the internal power voltage and the converted external power voltages, respectively, said input power select circuit monitoring the converted external voltage, selecting and outputting said first external power voltage when said first external power voltage is larger than a threshold voltage, selecting and outputting the internal power voltage when said first external power voltage is smaller than the threshold voltage, said selection of voltage facilitating seamless switching between the internal power voltage and the first converted external power voltage;
(b) a main bus switch in electrical communication with the input power select circuit to receive the selected voltage, the main bus switch controlling application of the selected voltage to the load of medical and utility devices; and
(c) a main bus in electrical communication with the main bus switch for transporting the selected voltage to the load of medical and utility devices.

13. The electrical power system as recited in claim 12 wherein the input power select circuit comprises a boost regulator circuit for creating an enhancement voltage that is greater than the selected voltage by a fixed amount of voltage and for controlling the state of the main bus switch using the enhanced selected voltage.

14. The electrical power system as recited in claim 13 wherein the boost regulator circuit creates an enhancement voltage from the selected voltage that is approximately 12 volts greater than the selected voltage.

15. The electrical power system as recited in claim 13 wherein the input power select circuit comprises:
(a) a diode OR gate for isolating and monitoring the converted external power voltages and outputting only one converted external power voltage at a given time; and
(b) a battery control circuit in electrical communication with the diode OR gate, said battery control circuit comparing the diode OR gate output with a threshold voltage, and enabling the rechargeable internal power source to output the internal power voltage to said bus switch when the diode OR gate output is smaller than the threshold voltage.

16. The electrical power system as recited in claim 12 wherein the threshold voltage is set at approximately six volts less than nominal value of a converted external power voltage, allowing the input power select circuit to switch to select the internal power voltage while a residual voltage due to capacitance discharge of a corresponding power converter and main bus load still remains on the main bus, resulting in uninterrupted electrical power to the load of medical and utility devices.

17. The electrical power system as recited in claim 12 wherein the bus switch comprises a field-effect transistor switch.

18. The electrical power system as recited in claim 12 further comprises a main bus delay circuit for controlling the state of the main bus switch, the main bus delay circuit receiving the selected voltage and controlling the state of the main bus switch to delay application of the selected voltage to the main bus by an amount of time at initial power-up to prevent fire hazard due to flammable gas build-up in the transportable life support system.

19. A switching control circuit for use in an electrical power system for a transportable life support system, the switching control circuit providing uninterrupted electrical power to a load of medical and utility devices by switching between one of a set of converted external power sources, provided by one of a set of power converters, and an internal power voltage outputted by a rechargeable internal power source, the switching control circuit comprising:
(a) an input power select circuit in electrical communication with the rechargeable internal power source and with the power converters to receive the internal power voltage and the converted external power voltage, respectively, said input power select circuit monitoring the converted external voltage and then selecting and outputting said external power voltage when said external power voltage is larger than a threshold voltage, selecting and outputting the internal power voltage when said external power voltage is smaller than the threshold voltage, said selection of voltage facilitating seamless switching between the internal power voltage and one of the converted external power voltages; and
(b) a main bus switch in electrical communication with the input power select circuit to receive the selected voltage, the main bus switch controlling application of the selected voltage to the load of medical and utility devices;
(c) a main bus in electrical communication with the bus switch for transporting the selected voltage to the load of medical and utility devices;
(d) wherein the input power select circuit comprises a boost regulator circuit for creating an enhancement voltage that is greater than the selected voltage by a fixed amount of voltage and for controlling the state of the main bus switch using the enhanced voltage.

20. A switching control circuit for use in an electrical power system for a transportable life support system, the switching control circuit providing uninterrupted electrical power to a load of medical and utility devices by switching between one of a set of converted external power sources, provided by one of a set of power converters, and an internal power voltage outputted by a rechargeable internal power source, the switching control circuit comprising:

(a) an input power select circuit in electrical communication with the rechargeable internal power source and with the power converters to receive the internal power voltage and the converted external power voltage, respectively, said input power select circuit monitoring the converted external voltage and then selecting and outputting said external power voltage when said external power voltage is larger than a threshold voltage, selecting and outputting the internal power voltage when said external power voltage is smaller than the threshold voltage, said selection of voltage facilitating seamless switching between the internal power voltage and one of the converted external power voltages;

(b) a main bus switch in electrical communication with the input power select circuit to receive the selected voltage, the main bus switch controlling application of the selected voltage to the load of medical and utility devices; and (c) a main bus in electrical communication with the bus switch for transporting the selected voltage to the load of medical and utility devices;

(d) wherein the input power select circuit comprises:
1. a diode OR gate for isolating and monitoring the converted external power voltages, only one of the converted voltages being active at a given time, the diode OR gate being operative to isolate the active converted voltage from the passive converted voltage; and
2. a battery control circuit in electrical communication with the one active converted voltage through a diode OR gate, said battery control circuit comparing the diode OR gate output with a threshold voltage, and enabling the rechargeable internal power source to output the internal power voltage to said bus switch when the diode OR gate output is smaller than the threshold voltage.

21. A switching control circuit for use in an electrical power system for a transportable life support system, the switching control circuit providing uninterrupted electrical power to a load of medical and utility devices by switching between one of a set of converted external power sources, provided by one of a set of power converters, and an internal power voltage outputted by a rechargeable internal power source, the switching control circuit comprising:

(a) an input power select circuit in electrical communication with the rechargeable internal power source and with the power converters to receive the internal power voltage and the converted external power voltage, respectively, said input power select circuit monitoring the converted external voltage and then selecting and outputting said external power voltage when said external power voltage is larger than a threshold voltage, selecting and outputting the internal power voltage when said external power voltage is smaller than the threshold voltage, said selection of voltage facilitating seamless switching between the internal power voltage and one of the converted external power voltages; and (b) a main bus switch in electrical communication with the input power select circuit to receive the selected voltage, the main bus switch controlling application of the selected voltage to the load of medical and utility devices;

(c) a main bus in electrical communication with the bus switch for transporting the selected voltage to the load of medical and utility devices;

(d) wherein the threshold voltage, is set at approximately six volts less than nominal value of a converted external power voltage, allowing the input power select circuit to switch to select the internal power voltage while a residual voltage due to capacitance discharge of a corresponding power converter and main bus load remains on the main bus, resulting in uninterrupted electrical power to the load of medical and utility devices during voltage switching.

22. A switching control circuit for use in an electrical power system for a transportable life support system, the switching control circuit providing uninterrupted electrical power to a load of medical and utility devices by switching between one of a set of converted external power sources, provided by one of a set of power converters, and an internal power voltage outputted by a rechargeable internal power source, the switching control circuit comprising:

(a) an input power select circuit in electrical communication with the rechargeable internal power source and with the power converters to receive the internal power voltage and the converted external power voltage, respectively, said input power select circuit monitoring the converted external voltage and then selecting and outputting said external power voltage when said external power voltage is larger than a threshold voltage, selecting and outputting the internal power voltage when said external power voltage is smaller than the threshold voltage, said selection of voltage facilitating seamless switching between the internal power voltage and one of the converted external power voltages;

(b) a main bus switch in electrical communication with the input power select circuit to receive the selected voltage, the main bus switch controlling application of the selected voltage to the load of medical and utility devices;

(c) a main bus in electrical communication with the bus switch for transporting the selected voltage to the load of medical and utility devices; and (d) a main bus delay circuit for controlling the state of the main bus switch, the main bus delay circuit receiving the selected voltage and controlling the state of the main bus switch to delay application of the selected voltage to the main bus by a fixed amount of time at initial power-up to prevent fire hazard due to flammable gas build-up in the transportable life system.

* * * * *